United States Patent
Shimoda et al.

(10) Patent No.: US 10,653,356 B2
(45) Date of Patent: May 19, 2020

(54) TRAINING APPARATUS, TRAINING METHOD, AND PROGRAM

(71) Applicant: TOYOTA JIDOSHA KABUSHIKI KAISHA, Toyota-shi, Aichi-ken (JP)

(72) Inventors: Shingo Shimoda, Kasugai (JP); Fady S K Shibata Alnajjar, Nagoya (JP); Tytus Wojtara, Chiba (JP); Hitoshi Yamada, Nagakute (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 14/511,542

(22) Filed: Oct. 10, 2014

(65) Prior Publication Data
US 2015/0106023 A1    Apr. 16, 2015

(30) Foreign Application Priority Data
Oct. 11, 2013   (JP) ................. 2013-213327

(51) Int. Cl.
| | |
|---|---|
| A61B 5/00 | (2006.01) |
| A61B 5/0488 | (2006.01) |
| G16H 20/00 | (2018.01) |
| G16H 20/30 | (2018.01) |
| A61H 1/02 | (2006.01) |

(52) U.S. Cl.
CPC ......... *A61B 5/4519* (2013.01); *A61B 5/0488* (2013.01); *A61B 5/7246* (2013.01); *G16H 20/00* (2018.01); *G16H 20/30* (2018.01); *A61B 5/7275* (2013.01); *A61B 2505/09* (2013.01); *A61H 1/02* (2013.01); *A61H 2230/60* (2013.01)

(58) Field of Classification Search
None
See application file for complete search history.

(56) References Cited

FOREIGN PATENT DOCUMENTS

WO    98/46129 A1    10/1998

OTHER PUBLICATIONS

F Hug, NA Turpin, A Guevel, S Dorel. Is interindividual variability of EMG patterns in trained cyclists related to different muscle synergies. J Appl Physiol 2010, vol. 108, p. 1727-1736.*

(Continued)

*Primary Examiner* — Olivia M. Wise
(74) *Attorney, Agent, or Firm* — Oliff PLC (57) ABSTRACT

A training apparatus includes: a controller. The controller is configured to: (a) while a subject is performing a behavior, acquire time-series myoelectric potentials of each of muscles of the subject; (b) calculate a muscle synergy matrix W, a control matrix C and an error matrix E from a myoelectric potential matrix M so that the relationship M=WC+E is satisfied, row vectors each expressing the acquired time-series myoelectric potentials of a corresponding one of the muscles, m being arranged in rows in the myoelectric potential matrix, n unit column vectors being arranged in columns in the muscle synergy matrix W, n row vectors being arranged in rows in the control matrix; (c) calculate a feature quantity indicating consistency among the unit column vectors included in the calculated muscle synergy matrix W; and (d) output the calculated feature quantity.

12 Claims, 3 Drawing Sheets

(56) References Cited

OTHER PUBLICATIONS

Brendan O'Connor. Cosine similarity, Pearson correlation coefficient, and OLS coefficients. Al and Social Science. Mar. 13, 2012. p. 1-7.*

DJ Clark, LH Ting, FE Zajac, RR Neptune, SA Kautz. Merging of Healthy Motor Modules Predicts Reduced Locomotor Performance and Muscle Coordination Complexity Post-Stroke. J Neurophysiol 2010, vol. 103, p. 844-857.*

VCK Cheung, A Turolla, M Agostini, S Silvoni, C Bennis, p. Kasi, S Paganoni, P Bonato, E Bizzi. Muscle synergy patterns as physiological markers of motor cortical damage. PNAS Sep. 4, 2012, vol. 109, No. 36, p. 14652-14656.*

B Salman, S Vandat, O Lambercy, L Dovat, E Burdet, T Milner. Changes in Muscle Activation Patterns Following Robot-assisted Training of Hand Function after Stroke. The 2010 IEEE/RSJ International Conference on Intelligent Robots and Systems. Oct. 18-22, 2010, Taipei, Taiwan. 5145-5150.*

Criswell. Chapter 8, Dynamic Assessment. Cram's Introduction to surface electromyography, 2nd edition. Jones and Bartlett Publishers. pp. 123-140 (Year: 2011).*

Kawasaki et al. "Development of a hand motion assist robot for rehabilitation therapy by patient self-motion control." In Rehabilitation Robotics, ICORR 2007. IEEE 10th International Conference, p. 234-240 (Year: 2007).*

De Kroon et al. Electrical Stimulation of the upper extremity in stroke: cyclic versus EMG-triggered stimuation. Clinical Rehabilitation 2008, vol. 22, pp. 690-697 (Year: 2008).*

Mavroidis et al. Smart portable rehabilitation devices. Journal of NeuroEngineering and Rehabilitation. 2005, vol. 2, No. 18, pp. 1-15 (Year: 2005).*

Sinkjaer et al. Biopotentials as command and feedback signals in functional electrical stimulation systems. Medical Engineering & Physics. 2003, vol. 25, pp. 29-40 (Year: 2003).*

Francisco et al. Electromyogram-Triggered Neuromuscular Stimulation for Improving the Arm Function of Acute Stroke Survivors: A Randomized Pilot Study. Arch Phys Med Rehabil 1998, vol. 79, pp. 570-575. (Year: 1998).*

Bolton et al. Electromyogram-triggered neuromuscular stimulation and stroke motor recovery of arm/hand functions: a meta-analysis. Journal of Neurological Sciences, 223, pp. 121-127 (Year: 2004).*

Cheung et al., "Muscle Synergy Patterns as Physiological Markers of Motor Cortical Damage," *PNAS*, Sep. 4, 2012, vol. 109, No. 36, pp. 14652-14656.

Turpin et al., "Effect of Power Output on Muscle Coordination During Rowing", European Journal of Applied Physiology, Mar. 31, 2011, pp. 3017-3029, vol. 111, No. 12, Springer, Berlin.

Alnajjar et al., "A Bio-Inspired Neuromuscular Model to Simulate the Neuro-Sensorimotor Basis for Postural-Reflex-Response in Humans", 4th IEEE RAS&EMBS International Conference on Biomedical Robotics and Biomechatronics, Jun. 24, 2012, pp. 980-985.

* cited by examiner

TRAINING APPARATUS, TRAINING METHOD, AND PROGRAM

INCORPORATION BY REFERENCE

The disclosure of Japanese Patent Application No. 2013-213327 filed on Oct. 11, 2013 including the specification, drawings and abstract is incorporated herein by reference in its entirety.

BACKGROUND OF THE INVENTION

1. Field of the Invention

The invention relates to a training apparatus and training method suitable for determining a proficiency level of a subject in a behavior or a task consisting of one or more behaviors on the basis of time-series myoelectric potentials that are acquired while the subject is performing the behavior or the task consisting of one or more behaviors, and a program for causing a computer to execute functions of the training apparatus.

2. Description of Related Art

Researches for the workings of a central nervous system that controls a plurality of muscles have been pursued so far. For example, as described in Vincent C. K. Cheung, Andrea Turolla, Michela Agostini, Stefano Silvoni, Caoimhe Bennis, Patrick Kasi, Sabrina Paganoni, Paolo Bonato, and Emilio Bizzi, Muscle synergy patterns as physiological markers of motor cortical damage, PNAS, vol. 109, no. 36, pp. 14652-14656, dated Sep. 4, 2012, when a human performs a behavior or performs a task consisting of one or more behaviors, there arises a phenomenon called muscle synergy in which a plurality of muscles cooperatively work with redundancy.

Here, a feature quantity is obtained. The feature quantity is used to objectively determine how much a patient who requires rehabilitation because of an injury or a disease is able to perform a behavior or a task with which the patient is charged. In obtaining the feature quantity, it is required to consider the phenomenon called muscle synergy in the central nervous system of a human.

SUMMARY OF THE INVENTION

The invention provides a training apparatus and training method suitable for determining a proficiency level of a subject in a behavior or a task consisting of one or more behaviors on the basis of time-series myoelectric potentials that are acquired while the subject is performing the behavior or the task consisting of one or more behaviors, and a non-transitory computer-readable information storage medium storing a program for causing a computer to execute functions of the training apparatus.

A first aspect of the invention provides a training apparatus. The training apparatus includes a controller. The controller is configured to: (a) while a subject is performing a behavior, acquire time-series myoelectric potentials of each of muscles 1, 2, . . . , m of the subject; (b) calculate a muscle synergy matrix W, a control matrix C and an error matrix E from a myoelectric potential matrix M so that the relationship $M=WC+E$ is satisfied, row vectors each expressing the acquired time-series myoelectric potentials of a corresponding one of the muscles 1, 2, . . . , m being arranged in rows in the myoelectric potential matrix M, n unit column vectors $W^{(1)}, W^{(2)}, \ldots, W^{(n)}$ being arranged in columns in the muscle synergy matrix W, n row vectors $C^{(1)}, C^{(2)}, \ldots, C^{(n)}$ being arranged in rows in the control matrix C; (c) calculate a feature quantity indicating consistency among the unit column vectors $W^{(1)}, W^{(2)}, \ldots, W^{(n)}$ included in the calculated muscle synergy matrix W; and (d) output the calculated feature quantity.

In the training apparatus according to the above aspect, the controller may be configured to apply non-negative matrix factorization, and the feature quantity may be an SCI that is calculated through computation of inner product $p(x,y)$ of row vectors x, y as $SCI=2/[n(n+2)] \times \Sigma_{i=1}^{n} \Sigma_{j=1, j \neq i}^{n} p(W^{(i)}, W^{(j)})$.

In the training apparatus according to the above aspect, the controller may be configured to output, to the subject, the fact that the SCI is larger than or equal to a predetermined threshold.

A second aspect of the invention provides a training apparatus. The training apparatus includes a controller. The controller is configured to: (e) while a subject is performing a task consisting of behaviors k=1, 2, . . . , p, acquire time-series myoelectric potentials of each of muscles 1, 2, . . . , m of the subject; (f) calculate a muscle synergy matrix $W_k$, a control matrix $C_k$ and an error matrix $E_k$ from a myoelectric potential matrix $M_k$ for each of the behaviors k=1, 2, . . . , p so that the relationship $M_k=W_k C_k+E_k$ is satisfied, row vectors each expressing the acquired time-series myoelectric potentials of a corresponding one of the muscles 1, 2, . . . , m being arranged in rows in the myoelectric potential matrix $M_k$, n unit column vectors $W_k^{(1)}, W_k^{(2)}, \ldots, W_k^{(n)}$ being arranged in columns in the muscle synergy matrix $W_k$, n row vectors $C_k^{(1)}, C_k^{(2)}, \ldots, C_k^{(n)}$ being arranged in rows in the control matrix $C_k$; (g) calculate a feature quantity indicating consistency among the unit column vectors $W_1^{(1)}, W_2^{(1)}, \ldots, W_p^{(1)}$ consistency among the unit column vectors $W_1^{(2)}, W_2^{(2)}, \ldots, W_p^{(2)}, \ldots$, consistency among the unit column vectors $W_1^{(n)}, W_2^{(n)}, \ldots, W_p^{(n)}$, these unit column vectors $W_1^{(1)}, W_2^{(1)}, \ldots, W_p^{(1)}$, unit column vectors $W_1^{(2)}, W_2^{(2)}, \ldots, W_p^{(2)}, \ldots$, and unit column vectors $W_1^{(n)}, W_2^{(n)}, \ldots, W_p^{(n)}$ being included in the calculated muscle synergy matrices $W_1, W_2, \ldots, W_p$; and (h) output the calculated feature quantity.

In the training apparatus according to the above aspect, the controller may be configured to apply non-negative matrix factorization, and the feature quantity may be an SSI that is calculated through computation of correlation coefficient $r(x,y)$ of vectors x, y as $SSI=2[n \times p(p-1)] \times \Sigma_{i=1}^{n} \Sigma_{k=1}^{p} \Sigma_{h=1, h \neq k}^{p} r(W_k^{(i)}, W_h^{(i)})$.

In the training apparatus according to the above aspect, the controller may be configured to output, to the subject, one of the fact that the SSI is larger than or equal to a predetermined threshold and the fact that the SSI tends to increase with an increase in the p indicating the number of the behaviors.

A third aspect of the invention provides a training apparatus. The training apparatus includes a controller. The controller is configured to: (i) while a subject is performing a task consisting of behaviors k=1, 2, . . . , p, acquire time-series myoelectric potentials of each of muscles 1, 2, . . . , m of the subject; (j) calculate a muscle synergy matrix $W_k$, a control matrix $C_k$ and an error matrix $E_k$ from a myoelectric potential matrix $M_k$ for each of the behaviors k=1, 2, . . . , p so that the relationship $M_k=W_k C_k+E_k$ is satisfied, row vectors each expressing the acquired time-series myoelectric potentials of a corresponding one of the muscles 1, 2, . . . , m being arranged in rows in the myoelectric potential matrix $M_k$, n unit column vectors $W_k^{(1)}, W_k^{(2)}, \ldots, W_k^{(n)}$ being arranged in columns in the muscle synergy matrix $W_k$, n row vectors $C_k^{(1)}, C_k^{(2)}, \ldots, C_k^{(n)}$ being arranged in rows in the control matrix $C_k$; (k) calculate a feature quantity indicating consistency among the row vectors $C_1^{(1)}, C_2^{(1)}, \ldots, C_p^{(1)}$, consistency among the row vectors $C_1^{(2)}, C_2^{(2)}, \ldots, C_p^{(2)}, \ldots$, consistency among the row vectors $C_1^{(n)}, C_2^{(n)}, \ldots, C_p^{(n)}$, these row vectors $C_1^{(1)}, C_2^{(1)}, C_p^{(1)}$, row vectors $C_1^{(2)}, C_2^{(2)}, \ldots, C_p^{(2)}, \ldots$, and row vectors $C_1^{(n)}, C_2^{(n)}, \ldots, C_p^{(n)}$ being included in the calculated control matrices $C_1, C_2, \ldots, C_p$; and (l) output the calculated feature quantity.

In the training apparatus according to the above aspect, the controller may be configured to apply non-negative matrix factorization, and the feature quantity may be an $SSI_C$ that is calculated through computation of correlation coefficient $r(x,y)$ of vectors $x$, $y$ as $SSI_C = 2/[n \times p(p-1)] \times \Sigma_{i=1}^{n} \Sigma_{k=1}^{p} \Sigma_{h=1, h \neq k}^{p} r(C_k^{(i)}, C_h^{(i)})$.

In the training apparatus according to the above aspect, the controller may be configured to output, to the subject, one of the fact that the $SSI_C$ is smaller than or equal to a predetermined threshold and the fact that the $SSI_C$ tends to decrease with an increase in the p indicating the number of the behaviors.

In the training apparatus according to the above aspect, the controller may be configured to calculate a right feature quantity for a muscle of a right side of a body of the subject and a left feature quantity for a muscle of a left side of the body of the subject, and the controller may be configured to output, to the subject, one of information about both the right feature quantity and the left feature quantity and information about a similarity between the right feature quantity and the left feature quantity.

A fourth aspect of the invention provides a training method for an apparatus including a controller. The training method includes: while a subject is performing a behavior, acquiring, by the controller, time-series myoelectric potentials of each of muscles 1, 2, . . . , m of the subject; calculating, by the controller, a muscle synergy matrix W, a control matrix C and an error matrix E from a myoelectric potential matrix M so that the relationship M=WC+E is satisfied, row vectors each expressing the acquired time-series myoelectric potentials of a corresponding one of the muscles 1, 2, . . . , m being arranged in rows in the myoelectric potential matrix M, n unit column vectors $W^{(1)}, W^{(2)}, \ldots, W^{(n)}$ being arranged in columns in the muscle synergy matrix W, n row vectors $C^{(1)}, C^{(2)}, \ldots, C^{(n)}$ being arranged in rows in the control matrix C; calculating, by the controller, a feature quantity indicating consistency among the unit column vectors $W^{(1)}, W^{(2)}, \ldots, W^{(n)}$ included in the calculated muscle synergy matrix W; and outputting, by the controller, the calculated feature quantity.

A fifth aspect of the invention provides a training method for an apparatus including a controller. The training method includes: while a subject is performing a task consisting of behaviors k=1, 2, . . . , p, acquiring, by the controller, time-series myoelectric potentials of each of muscles 1, 2, . . . , m of the subject; calculating, by the controller, a muscle synergy matrix $W_k$, a control matrix $C_k$ and an error matrix $E_k$ from a myoelectric potential matrix $M_k$ for each of the behaviors k=1, 2, . . . , p so that the relationship $M_k=W_kC_k+E_k$ is satisfied, row vectors each expressing the acquired time-series myoelectric potentials of a corresponding one of the muscles 1, 2, . . . , m being arranged in rows in the myoelectric potential matrix $M_k$, n unit column vectors $W_k^{(1)}, W_k^{(2)}, \ldots, W_k^{(n)}$ being arranged in columns in the muscle synergy matrix $W_k$, n row vectors $C_k^{(1)}, C_k^{(2)}, \ldots, C_k^{(n)}$ being arranged in rows in the control matrix $C_k$; calculating, by the controller, a feature quantity indicating consistency among the unit column vectors $W_1^{(1)}, W_2^{(1)}, \ldots, W_p^{(1)}$, consistency among the unit column vectors $W_1^{(2)}, W_2^{(2)}, \ldots, W_p^{(2)}, \ldots$, consistency among the unit column vectors $W_1^{(n)}, W_2^{(n)}, \ldots, W_p^{(n)}$, these unit column vectors $W_1^{(1)}, W_2^{(1)}, \ldots, W_p^{(1)}$, unit column vectors $W_1^{(2)}, W_2^{(2)}, \ldots, W_p^{(2)}$, and unit column vectors $W_1^{(n)}, W_2^{(n)}, \ldots, W_p^{(n)}$ being included in the calculated muscle synergy matrices $W_1, W_2, \ldots, W_p$; and outputting, by the controller, the calculated feature quantity.

A sixth aspect of the invention provides a training method for an apparatus including a controller. The training method includes: while a subject is performing a task consisting of behaviors k=1, 2, . . . , p, acquiring, by the controller, time-series myoelectric potentials of each of muscles 1, 2, . . . , m of the subject; calculating, by the controller, a muscle synergy matrix $W_k$, a control matrix $C_k$ and an error matrix $E_k$ from a myoelectric potential matrix $M_k$ for each of the behaviors k=1, 2, . . . , p so that the relationship $M_k=W_kC_k+E_k$ is satisfied, row vectors each expressing the acquired time-series myoelectric potentials of a corresponding one of the muscles 1, 2, . . . , m being arranged in rows in the myoelectric potential matrix $M_k$, n unit column vectors $W_k^{(1)}, W_k^{(2)}, \ldots, W_k^{(n)}$ being arranged in columns in the muscle synergy matrix $W_k$, n row vectors $C_k^{(1)}, C_k^{(2)}, \ldots, C_k^{(n)}$ being arranged in rows in the control matrix $C_k$; calculating, by the controller, a feature quantity indicating consistency among the row vectors $C_1^{(1)}, C_2^{(1)}, \ldots, C_p^{(1)}$, consistency among the row vectors $C_1^{(2)}, C_2^{(2)}, \ldots, C_p^{(2)}, \ldots$, consistency among the row vectors $C_1^{(n)}, C_2^{(n)}, \ldots, C_p^{(n)}$, these row vectors $C_1^{(1)}, C_2^{(1)}, \ldots, C_p^{(1)}$, row vectors $C_1^{(2)}, C_2^{(2)}, \ldots, C_p^{(2)}, \ldots$, and row vectors $C_1^{(n)}, C_2^{(n)}, \ldots, C_p^{(n)}$ being included in the calculated control matrices $C_1, C_2, \ldots, C_p$; and outputting, by the controller, the calculated feature quantity.

A seventh aspect of the invention provides a non-transitory computer-readable information storage medium storing a program for causing a computer to execute functions of any one of the above-described training apparatuses.

The computer-readable information storage medium according to the above aspect may be a compact disk, a flexible disk, a hard disk, a magneto-optical disk, a digital video disk, a magnetic tape, a semiconductor memory, or the like.

The program may be distributed or sold via a computer communication network independently of a computer on which the program is executed. The information storage medium may be distributed or sold independently of a computer or a digital signal processor.

According to the aspects of the invention, it is possible to provide a training apparatus and training method suitable for determining a proficiency level of a subject in a behavior or a task consisting of a plurality of behaviors on the basis of time-series myoelectric potentials that are acquired while the subject is performing the behavior or the task consisting of one or more behaviors, and a non-transitory computer-readable information storage medium storing a program for causing a computer to execute functions of the training apparatus.

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

Hereinafter, an embodiment of the invention will be described. The embodiment described below is only illustrative, and does not limit the scope of the invention. Therefore, although persons skilled in the art are able to employ embodiments in which part or all of elements of the embodiment are replaced with equivalent elements, the scope of the invention also encompasses those embodiments.

Figure 1:
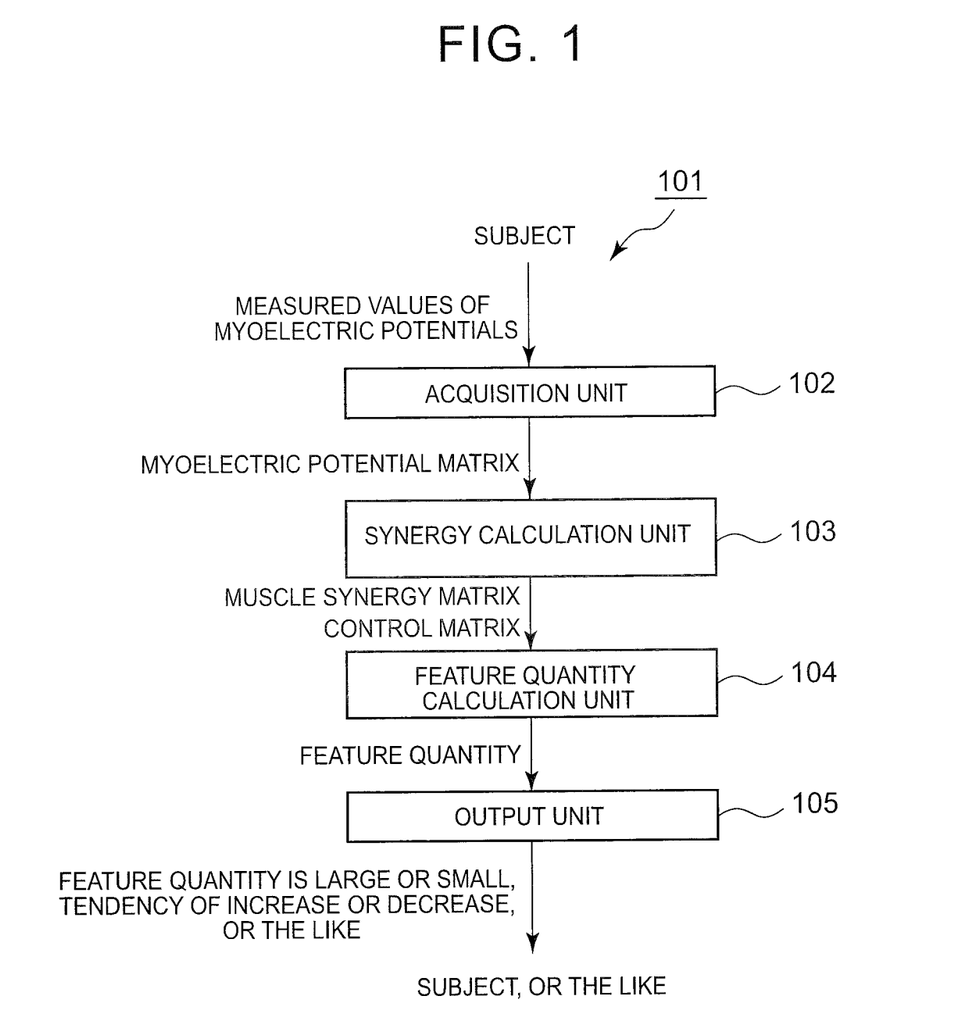
FIG. 1 is a view that illustrates the schematic configuration of a training apparatus.

FIG. 1 is a view that illustrates the schematic configuration of a training apparatus according to the present embodiment. Hereinafter, description will be made with reference to FIG. 1.

The training apparatus 101 according to the present embodiment includes an acquisition unit 102, a synergy calculation unit 103, a feature quantity calculation unit 104, and an output unit 105. The training apparatus 101 may be implemented by executing a predetermined program on a computer. Instead, the training apparatus 101 may be implemented by an exclusive electronic circuit or may be implemented by configuring software to hardware like a field programmable gate array (FPGA).

In the present embodiment, a proficiency level of a subject in a behavior or a task consisting of behaviors k=1, 2, . . . , p is calculated on the basis of myoelectric potentials acquired while the subject is performing the behavior or while the subject is performing the task, and the proficiency level is output.

For example, in the case of a subject who undergoes right hand rehabilitation, the subject may receive training for repeatedly bending and stretching his or her right wrist. In this training, single bending and stretching of the right wrist corresponds to a single behavior. When the subject repeats bending and stretching p times, the first bending and stretching, the second bending and stretching, . . . , the p-th bending and stretching respectively correspond to behavior 1, behavior 2, . . . , behavior p. Each behavior in a task should be typically the same; however, different behaviors may be included in a task.

Hereinafter, initially, the case where the proficiency level of the subject is calculated on the basis of time-series myoelectric potentials of each of muscles 1, 2, . . . , m, acquired while the subject is performing a behavior will be described.

Figure 2:
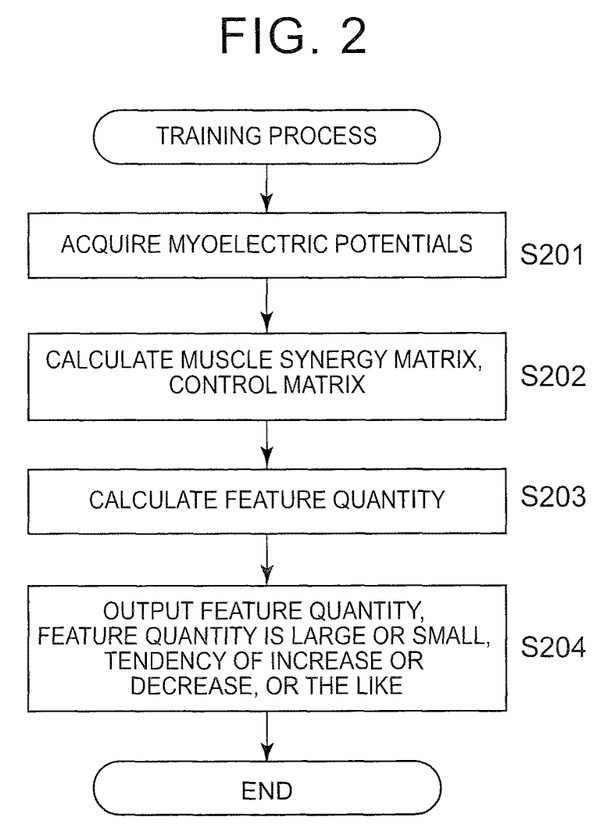
FIG. 2 is a view that shows a flowchart of control of a training process that is executed by the training apparatus.

FIG. 2 is a view that illustrates a flowchart of control of a training process that is executed by the training apparatus according to the present embodiment. Hereinafter, description will be made with reference to FIG. 2.

Initially, the acquisition unit 102 acquires time-series myoelectric potentials of each of the muscles 1, 2, . . . , m while the subject is performing a behavior (step S201). In the present embodiment, myoelectric potentials at m points of a body of the subject are measured. Points at which a myoelectric potential should be measured are muscles associated with the behavior (for example, bending and stretching of right hand) of a portion (for example, right hand) for training.

Measurement is performed from the start of a behavior to the end of the behavior at constant time intervals. A value of myoelectric potential of the i-th muscle at the j-th timing is stored in the i-th row and j-th column element M[i,j] of a myoelectric potential matrix M. That is, the myoelectric potential matrix M is configured such that a row vector M(1) consisting of time-series myoelectric potentials of the muscle 1, a row vector M(2) consisting of time-series myoelectric potentials of the muscle 2, . . . , and a row vector M(m) consisting of time-series myoelectric potentials of the muscle m are arranged in rows.

Thus, the number of rows of the myoelectric potential matrix M is m. The number of columns of the myoelectric potential matrix M changes with the time length of measurement, that is, the time length of a behavior, and the frequency or interval of measurement during the behavior.

In this way, when the myoelectric potential matrix M is acquired, the synergy calculation unit 103 calculates a muscle synergy matrix W, a control matrix C and an error matrix E so that M=WC+E (step S202). At this time, non-negative matrix factorization is used.

Hereinafter, for the sake of easy understanding, description will be made by omitting a suffix $_k$ where appropriate.

In non-negative matrix factorization, the degree of error is minimized or a similarity L is maximized.

Where the number of columns of the myoelectric potential matrix M, the number of columns of the control matrix C and the number of columns of the error matrix E all are t, the number of rows of the myoelectric potential matrix M, the number of rows of the muscle synergy matrix W and the number of rows of the error matrix E all are m, and the number of columns of the muscle synergy matrix W and the number of rows of the control matrix C all are n, the similarity L may be defined as follows.

$$L = 1 - 1/m \times \Sigma_{i=1}^{m} \sqrt{[\Sigma_{j=1}^{t} E[i,j]^2]} / \sqrt{[\Sigma_{j=1}^{t}(WC)[i,j]^2]}$$

Here, n is a numeric value that indicates the number of synergies. Generally, when n is increased, L also increases. An appropriate value of n may also be determined as follows by using non-negative matrix factorization as needed.

Generally, in non-negative matrix factorization, it is desired to select the number of synergies n so that the similarity L is higher than or equal to 70%. On the other hand, when the number of synergies n is too large, not only a calculation load increases but also over-adaptation occurs, with the result that an appropriate process is not executed on the contrary.

Therefore, the following method is used.

That is, for each of n=1, 2, 3, 4, . . . , the above-described similarity L is calculated.

Figure 3:
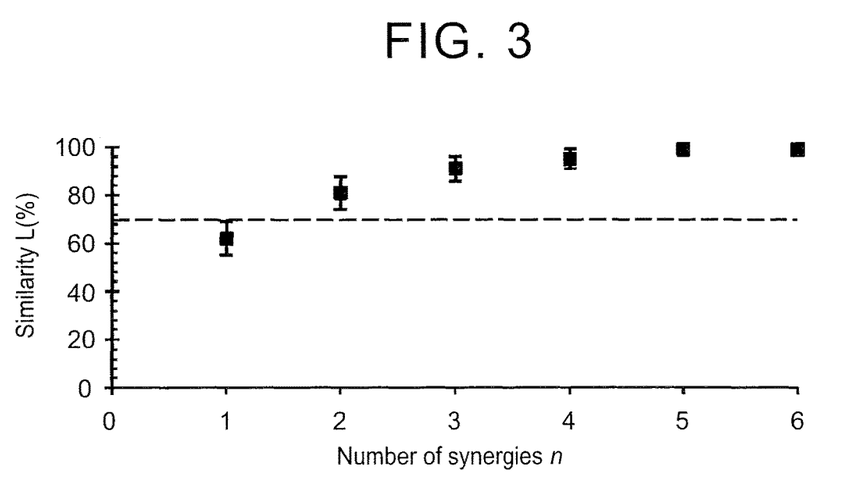
FIG. 3 is a graph that shows a similarity calculated at the number of synergies in a behavior.

FIG. 3 is a graph that shows the similarity L calculated for the number of synergies n for a behavior. Hereinafter, description will be made with reference to FIG. 3.

In FIG. 3, the abscissa axis Number of synergies n represents the number of synergies n, and the ordinate axis Similarity L (%) represents the similarity L. As shown in FIG. 3, it appears that, as the number of synergies n increases, the similarity L also increases; however, the degree of increase in similarity L is saturated at the number of synergies n of about 5, and the similarity L is higher than or equal to 70%. Thus, a numeric value before or after the beginning of saturation, for example, 4, 5 or 6, may be employed as the number of synergies n for the following calculation.

The number of synergies n may be a value different for each individual subject. Alternatively, the number of synergies n may be a value common to all the subjects because it is presumable that there is no large difference in the number of synergies when a human performs a behavior. In the latter case, some subjects are caused to perform a behavior experimentally in advance, an adequate value of n is determined by non-negative matrix factorization, and, thereafter, the determined value of n is directly used for the other subjects as well.

In this model, it is assumed that, when the central nerve of a subject supplies n control signals $C^{(1)}, C^{(2)}, \ldots, C^{(n)}$ to m muscles, the muscle 1 attempts to move so that the myoelectric potential $WC^{(1)}$ is satisfied, the muscle 2 attempts to move so that the myoelectric potential $WC^{(2)}$ is satisfied, . . . , and the muscle m attempts to move so that the myoelectric potential $WC^{(n)}$ is satisfied.

According to the researches of the inventors, as is shown as the experimental result later, the following result is obtained. That is, as the control signals $C^{(1)}, C^{(2)}, \ldots, C^{(n)}$ become independent of each other and become nonredundant as much as possible, that is, as unit column vectors $W^{(1)}, W^{(2)}, \ldots, W^{(n)}$ in the muscle synergy matrix W do not vary from one another and become consistent with one another, the workings of the central nerve in the behavior are good, and the proficiency level is high.

Therefore, the feature quantity calculation unit 104 calculates a feature quantity associated with the workings of the central nerve and the proficiency level on the basis of the control matrix C and the muscle synergy matrix W (step S203).

The fact that the unit column vectors $W^{(1)}, W^{(2)}, \ldots, W^{(n)}$ do not vary from one another and are consistent with one another means that an expanse of space expressed by the unit column vectors $W^{(1)}, W^{(2)}, \ldots, W^{(n)}$ is narrow. That is, an n-dimensional volume of an n-dimensional parallel polyhedron is small. In the n-dimensional parallel polyhedron, the length of each side is 1, and the direction of each side is any one of $W^{(1)}, W^{(2)}, \ldots,$ and $W^{(n)}$.

As the angle formed between any two of the unit column vectors W(1), W(2), . . . , W(n) deviates from a right angle, the unit column vectors $W^{(1)}, W^{(2)}, \ldots, W^{(n)}$ do not vary from one another and are consistent with one another.

Various quantities may be employed as a feature quantity that indicates that the unit column vectors $W^{(1)}, W^{(2)}, \ldots, W^{(n)}$ included in the muscle synergy matrix W for a behavior do not vary from one another and are consistent with one another.

For example, it is conceivable to utilize the inner product of vectors. An inner product p(x,y) of two vectors x, y may be defined as follows where elements of the vector x are denoted by x[1], x[2], . . . , x[u] and elements of the vector y are denoted by y[1], y[2], . . . , y[u].

$$p(x,y) = \Sigma_{i=1}^{u}(x[i] \times y[i])$$

As a result, a feature quantity SCI for the muscle synergy matrix W may be determined as follows.

$$SCI = 2/[n(n+2)] \times \Sigma_{i=1}^{n} \Sigma_{j=1, j \neq i}^{n} p(W^{(i)}, W^{(j)})$$

The feature quantity SCI is a numeric value that increases as a proficiency level in a behavior increases.

The output unit 105 outputs the thus calculated feature quantity (step S204), after which the process ends.

The feature quantity, such as the calculated SCI, may be output to a subject who performs rehabilitation, or the like, or may be output to a medical doctor, supervisor, trainer, or the like, of the subject.

As described above, the feature quantity SCI is a numeric value that increases as the proficiency level in a behavior increases. According to the researches of the inventors, it is found that the feature quantity SCI becomes a numeric value larger than or equal to a certain threshold for a healthy person.

On the other hand, in rehabilitation, it is considered to be better to provide a subject with feedback on the fact that the subject is performing a behavior well.

Therefore, when a subject in rehabilitation has performed a behavior, and a feature quantity SCI calculated for the behavior is larger than or equal to the above-described threshold, it is possible to cause the subject to know that training is going well by providing the subject with feedback on the fact that the calculated feature quantity SCI is larger than or equal to the threshold.

As a method of feedback, for example, a method of displaying a graph of the feature quantity SCI on a screen and changing the color of the graph when the feature quantity SCI becomes larger than or equal to the threshold, a method of applying electrical stimulation to a portion of a body in rehabilitation when the feature quantity SCI becomes larger than or equal to the threshold, a method of, when the feature quantity SCI becomes larger than or equal to the threshold, informing the fact by voice, and the like, may be employed. In addition, when the feature quantity SCI is smaller than the threshold, voice, an image, or the like, that causes a subject to actively undergo rehabilitation may be output.

When a subject undergoes rehabilitation with a task consisting of a repetition of the same behavior, an $SCI_k$ may be calculated as follows for each of behaviors k=1, 2, . . . , p included in the task.

$$SCI_k = 2[n(n+2)] \times \Sigma_{i=1}^{n} \Sigma_{j=1, j \neq i}^{n} p(W_k^{(i)}, W_k^{(j)})$$

As a result, when rehabilitation proceeds smoothly, $SCI_1$, $SCI_2$, . . . , $SCI_p$ for the corresponding behaviors are considered to tend to increase, and are considered to be saturated after certain results are obtained. Therefore, by sequentially calculating and outputting an SCI for each behavior, a subject is caused to confirm the results in the behavior and then caused to start the next behavior. Thus, it is possible to increase the effect of rehabilitation.

In the above-described example, description is made on the assumption that single bending and stretching of a right wrist is a behavior; instead, a repetition of bending and stretching of a right wrist may be assumed as a behavior. In this case, an SCI may be calculated by collectively interpreting the overall task consisting of a plurality of behaviors or an overall training menu consisting of a plurality of tasks as a single behavior. For example, the "SCI of overall rehabilitation in a certain day", or the like, may be calculated.

In this case, a change in SCI is accumulated day by day for a single subject, and it is presumable that a task or training menu that is currently carried out by the subject is appropriate when the SCI tends to increase. At the stage at which an increase in SCI is saturated, the task or training menu ends, and a new task or training menu is started. Thus, it is possible to objectively adjust the progress of rehabilitation.

In the above-described embodiment, an SCI is calculated as the feature quantity for a single behavior. In the following present embodiment, an SSI or an $SSI_C$ is calculated. An SSI or an $SSI_C$ is a feature quantity for a task consisting of behaviors k=1, 2, ..., p. Typically, the behaviors k=1, 2, ..., p included in a task should be the same action; however, they may be different actions.

The acquisition unit 102, as well as the above, acquires a myoelectric potential matrix $M_1$, a myoelectric potential matrix $M_2$, ..., a myoelectric potential matrix $M_p$ for the task consisting of p behaviors k=1, 2, ..., p (step S201). The myoelectric potential matrix $M_1$ consists of time-series myoelectric potentials of each of the muscles 1, 2, ..., m while the subject is performing behavior 1. The myoelectric potential matrix $M_2$ consists of time-series myoelectric potentials of each of the muscles 1, 2, ..., m while the subject is performing behavior 2. The myoelectric potential matrix $M_p$ consists of time-series myoelectric potentials of each of the muscles 1, 2, ..., m while the subject is performing behavior p.

The number of rows of each of the myoelectric potential matrices $M_1, M_2, \ldots, M_p$ acquired here all are m; however, the number of columns of each of the myoelectric potential matrices $M_1, M_2, \ldots, M_p$ may be different depending on the time length of each of the behaviors.

Subsequently, the synergy calculation unit 103, as well as the above, calculates muscle synergy matrices $W_k$, control matrices $C_k$ and error matrices $E_k$ so that the relationship $M_k = W_k C_k + E_k$ (k=1, 2, ..., p) is satisfied (step S202).

When the proficiency level in a behavior increases by repeating the behavior, it is presumable that the muscle synergy matrices $W_1, W_2, \ldots, W_p$ gradually become unchanged.

Therefore, when the proficiency level increases, the unit column vectors respectively included in the same positions of the muscle synergy matrices $W_1, W_2, \ldots, W_p$ gradually become consistent and do not vary.

An SSI is a feature quantity that indicates the degree of consistency among the unit column vectors respectively included in the same positions of the muscle synergy matrices $W_1, W_2, \ldots, W_p$.

On the other hand, even when the behavior is repeated, the state or environment of the subject changes momently. Thus, the control signals that are respectively applied to the synergies do not gradually become consistent but may significantly vary in response to the change.

Therefore, on the contrary to the fact that the column vectors respectively included in the same positions of the muscle synergy matrices $W_1, W_2, \ldots, W_p$ gradually become consistent, the row vectors respectively included in the same positions of the control matrices $C_1, C_2, \ldots, C_p$ vary.

An $SSI_C$ is a feature quantity that indicates the degree of consistency among the row vectors that are respectively included in the same positions of the control matrices $C_1, C_2, \ldots, C_p$.

In the following description, the average e(x) of the elements included in the vector x, the variance v(x) of the elements included in the vector x, the standard deviation s(x) of the elements included in the vector x and computation of correlation coefficient r(x,y) of the two vectors x, y may be defined as follows where the elements of the vector x are denoted by x[1], x[2], ..., x[u] and the elements of the vector y are denoted by y[1], y[2], ..., y[u].

$$e(x) = (1/u) \times \Sigma_{i=1}^{u} x[i]$$

$$v(x) = (1u) \times \Sigma_{i=1}^{u} (x[i] - e(x))^2$$

$$s(x) = v(x)^{1/2}$$

$$r(x,y) = \Sigma_{i=1}^{u} (x[i] - e(x)) \times (y[i] - e(y)) [m \times s(x) \times s(y)]$$

The feature quantity calculation unit 104 calculates the feature quantity SSI or the feature quantity $SSI_C$ as follows.

$$SSI = 2/[n \times p(p-1)] \times \Sigma_{k=i}^{n} \Sigma_{k=1}^{p} \Sigma_{h=1}^{p}{}_{,h=k} r(W_k^{(i)}, W_h^{(i)})$$

$$SSI_C = 2/[n \times p(p-1)] \times \Sigma_{i=1}^{n} \Sigma_{k=1}^{p} \Sigma_{h=1}^{p}{}_{,h=k} r(C_k^{(i)}, C_h^{(i)})$$

As described above, it is presumable that, as the SSI increases, consistency among the unit column vectors $W_1^{(1)}, W_2^{(1)}, \ldots, W_p^{(1)}$, consistency among the unit column vectors $W_1^{(2)}, W_2^{(2)}, \ldots, W_p^{(2)}, \ldots$, and consistency among the unit column vectors $W_1^{(n)}, W_2^{(n)}, \ldots, W_p^{(n)}$ increase, and the proficiency level increases.

On the other hand, it is presumable that, as the $SSI_C$ decreases, variations among the row vectors $C_1^{(1)}, C_2^{(1)}, \ldots, C_p^{(1)}$, variations among the row vectors $C_1^{(2)}, C_2^{(2)}, \ldots, C_p^{(2)}$, and variations among the row vectors $C_1^{(n)}, C_2^{(n)}, \ldots, C_p^{(n)}$ increase, that is, consistency among them decreases, and the proficiency level increases.

When a task is useful for a subject, it is presumable that, with an increase in p indicating the number of behaviors, the SSI tends to increase, and the $SSI_C$ tends to decrease.

Therefore, the output unit 105 outputs the feature quantity calculated as in the case of the above (step S204), after which the process ends.

In the present embodiment, at the stage at which the p-th behavior has been completed, the SSI and the $SSI_C$ may be calculated for the behaviors 1, 2, ..., p and then these may be output in graph, or the like, or, when the SSI is larger than or equal to a certain threshold or tends to increase and/or the $SCI_k$ is smaller than or equal to a certain threshold or tends to decrease, the subject may be informed of that fact by electrical stimulation, voice, or the like.

Together with the above, the $SCI_k$ may be output in graph, or the like, or, when the $SCI_k$ is larger than or equal to a certain threshold or tends to increase, the subject may be informed of that fact by electrical stimulation, voice, or the like.

Figure 4A:
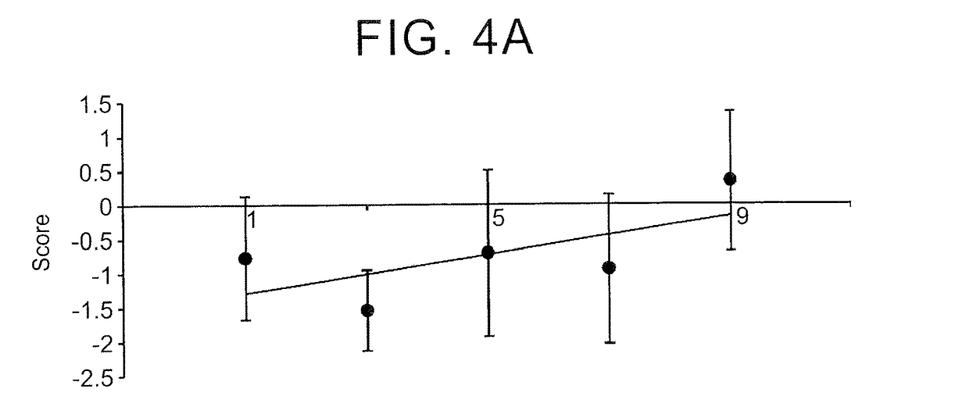
FIG. 4A is a graph that shows a change in score for a task when a subject has performed the task every other day.
Figure 4B:
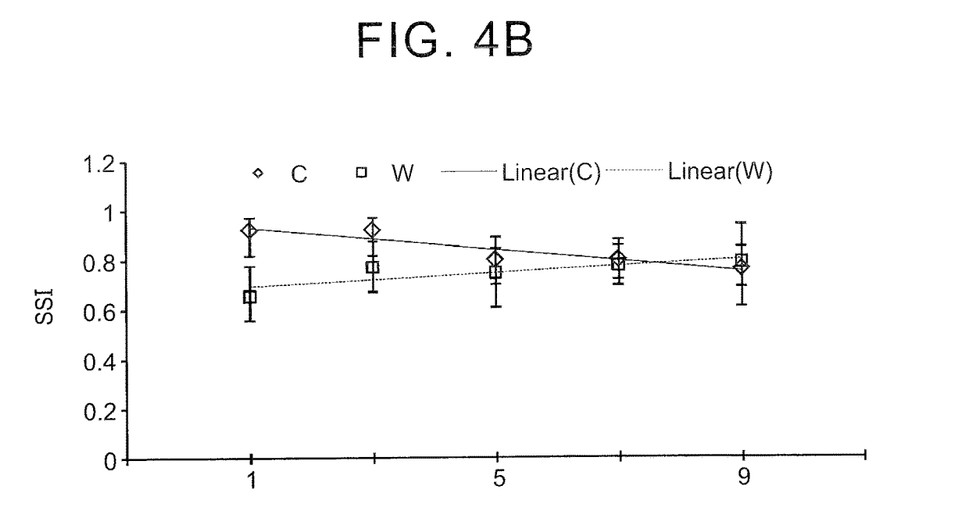
FIG. 4B is a graph that shows a change in SSI and a change in $SSI_C$ when the subject has performed a task every other day.
Figure 4C:
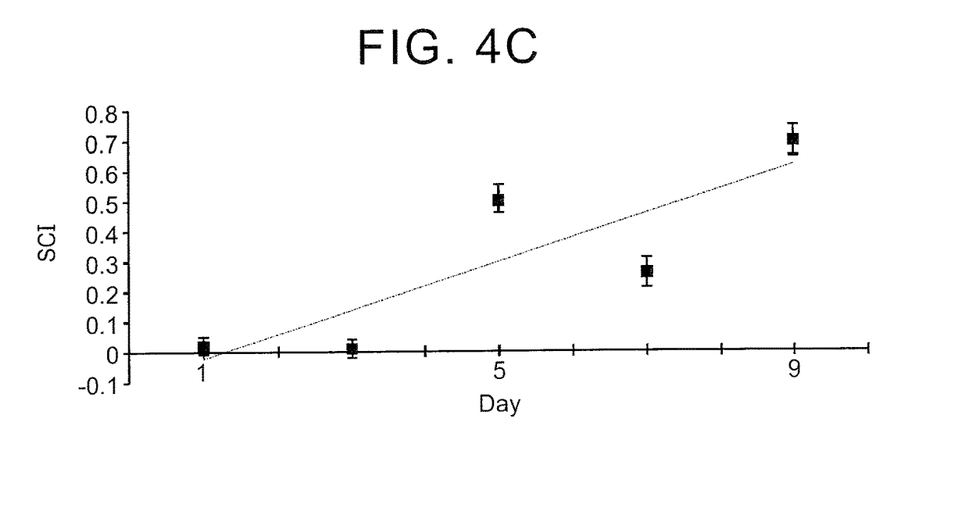
FIG. 4C is a graph that shows a change in SCI when the subject has performed a task every other day.

FIG. 4A, FIG. 4B and FIG. 4C are graphs that show changes in score, SSI, $SSI_C$, SCI to a task when a subject performs the task every other day. Hereinafter, description will be made with reference to FIG. 4A, FIG. 4B and FIG. 4C.

FIG. 4A is a graph in which the ordinate axis represents score and the abscissa axis represents elapsed days. The score is configured to increase when the subject has performed a predetermined action for a task with which the subject is charged and to decrease when the subject has failed to perform the predetermined action. It appears that the score tends to increase with the progress of rehabilitation.

FIG. 4B is a graph in which the ordinate axis represents SSI and $SSI_C$ and the abscissa axis represents elapsed days. It appears that the SSI(W) tends to increase and the $SSI_C$(C) tends to decrease with the progress of rehabilitation.

FIG. 4C is a graph in which the ordinate axis represents SCI and the abscissa axis represents elapsed days. It appears that the SCI tends to increase with the progress of rehabilitation.

In this way, assuming that a subject is caused to perform a task in rehabilitation, or the like, the subject initially has a low proficiency level.

When the subject repeatedly trains on a task consisting of one or more behaviors, it appears that the SSI increases and the $SSI_C$ decreases. It appears that the SCI of the overall task increases, and, in addition, $SCI_1, SCI_2, SCI_3, \ldots$ gradually increase for most of the behaviors included in the task.

That is, while these phenomena are observed, it means that the task is effectively functioning as an exercise for rehabilitation.

After that, when the subject gets sufficiently practiced at the task, the SSI, the $SSI_C$, the SCI and the $SCI_k$ do not change so much.

At this stage, it is allowed to further proceed with subject's rehabilitation by, for example, charging the subject with another task or changing the number of behaviors in the task. It is also allowed to determine that rehabilitation may be finished.

In this way, according to the present embodiment, it is possible to objectively understand how much the subject gets practiced at a task or behavior with which the subject is charged in rehabilitation.

In the above-described embodiment, electrical stimulation or voice is output on the basis of the result of comparison between the feature quantity, calculated at the time when a behavior or a task is performed, and the predetermined threshold or the tendency of increase or decrease in the feature quantity. In the present embodiment, output is performed by utilizing the fact that the body of a human is laterally symmetrical.

For example, assuming the case where a subject has a paralysis on one of the right side and left side of the body and the subject receives rehabilitation.

In the present embodiment, the subject is caused to try performing the same behavior or task on the right side and left side of the body at the same time. From laterally symmetrical measurement points, a right feature quantity for myoelectric potentials of the right side of the body and a left feature quantity for myoelectric potentials of the left side of the body are calculated through the method of calculating the feature quantity according to the above-described embodiment.

For example, when the subject has a paralysis at the right hand, the subject is caused to bend and stretch the right wrist and the left wrist at the same time. Measurement points are laterally symmetrically provided at the muscle of the right hand and the muscle of the left hand, the corresponding myoelectric potentials are measured, and then a feature quantity for the right hand and a feature quantity for the left hand are calculated.

When both the right side and left side of the body are healthy, it is presumable that the right feature quantity and the left feature quantity have substantially equal values.

Therefore, in the present embodiment, the right feature quantity and the left feature quantity are displayed in graph at the same time or the subject is provided with feedback by electrical stimulation, an image or voice on success of a behavior or task when the similarity between the right feature quantity and the left feature quantity is higher than or equal to a set value (when the difference between the right feature quantity and the left feature quantity is smaller than or equal to a set value). When the right feature quantity and the left feature quantity substantially coincide with each other, rehabilitation is sufficiently achieved.

According to the present embodiment, by doing a laterally symmetrical exercise as rehabilitation, it is possible to objectively determine the progress of rehabilitation without setting a threshold in advance.

According to the invention, it is possible to provide a training apparatus and training method suitable for determining a proficiency level of a subject in a behavior or a task consisting of a plurality of behaviors on the basis of time-series myoelectric potentials that are acquired while the subject is performing the behavior or the task consisting of the plurality of behaviors, and a program for causing a computer to execute functions of the training apparatus.

What is claimed is:

1. A training apparatus for rehabilitation, the apparatus comprising a processor configured to:
    simultaneously measure time-series myoelectric potentials of each of muscles 1, 2, ..., m for a right side of a body of a subject while measuring the time-series myoelectric potentials for a left side of the body of the subject while the subject is performing different behaviors, the different behaviors being included in a task including bending and stretching a right wrist and a left wrist of the subject;
    calculate a muscle synergy matrix W, a control matrix C and an error matrix E based on the acquired time-series myoelectric potentials and from a myoelectric potential matrix M so that a relationship M=WC+E is satisfied, row vectors each expressing the acquired time-series myoelectric potentials of one of the muscles 1, 2, ..., m being arranged in rows in the myoelectric potential matrix M, n unit column vectors $W^{(1)}$, $W^{(2)}$, ..., $W^{(n)}$ being arranged in columns in the muscle synergy matrix W, and n row vectors $C^{(1)}$, $C^{(2)}$, ..., $C^{(n)}$ being arranged in rows in the control matrix C;
    calculate a right feature quantity for a muscle of the right side of the body of the subject and a left feature quantity for a muscle of the left side of the body of the subject, the muscle of the right side of the body and the muscle of the left side of the body being selected from the muscles 1, 2, ... m;
    compare the right feature quantity with the left feature quantity and determine a rehabilitation progress of the subject based on the comparison, the comparison indicating consistency among the unit column vectors $W^{(1)}$, $W^{(2)}$, ..., $W^{(n)}$ included in the calculated muscle synergy matrix W; and
    provide the subject with feedback of progress of training based on the comparison between the right feature quantity and the left feature quantity, the feedback of progress being used to efficiently assess the rehabilitation progress, wherein providing the subject with the feedback of progress of training includes applying electrical stimulation to a portion of the body of the subject.

2. The training apparatus according to claim 1, wherein the processor is configured to apply non-negative matrix factorization, and the left feature quantity and the right feature quantity are each an SCI that are calculated through computation of inner product p(x,y) of row vectors x, y according to Expression I:

$$SCI=2/[n(n+2)]\times\Sigma_{i=1}^{n}\Sigma_{j=1,j\neq i}^{n}p(W^{(i)},W^{(j)}).$$ Expression I:

3. The training apparatus according to claim 2, wherein the processor is configured to output, to the subject, the fact that the SCI is larger than or equal to a predetermined threshold.

4. A training apparatus for rehabilitation, the apparatus comprising a processor configured to:
    simultaneously measure time-series myoelectric potentials of each of muscles 1, 2, ..., m for a right side of a body of a subject while measuring the time-series myoelectric potentials for a left side of the body of the subject while the subject is performing a task consisting of different behaviors k=1, 2, ..., p, the task including bending and stretching a right wrist and a left wrist of the subject;

calculate a muscle synergy matrix $W_k$, a control matrix $C_k$ and an error matrix $E_k$ based on the acquired time-series myoelectric potentials and from a myoelectric potential matrix $M_k$ for each of the behaviors k=1, 2, ..., p so that a relationship $M_k = W_k C_k + E_k$ is satisfied,
  row vectors each expressing the acquired time-series myoelectric potentials of a corresponding one of the muscles 1, 2, ..., m being arranged in rows in the myoelectric potential matrix $M_k$, n unit column vectors $W_k^{(1)}, W_k^{(2)}, \ldots, W_k^{(n)}$ being arranged in columns in the muscle synergy matrix $W_k$, n row vectors $C_k^{(1)}, C_k^{(2)}, \ldots, C_k^{(n)}$ being arranged in rows in the control matrix $C_k$;
calculate a right feature quantity for a muscle of the right side of the body of the subject and a left feature quantity for a muscle of the left side of the body of the subject, the muscle of the right side of the body and the muscle of the left side of the body being selected from the muscles 1, 2, ... m;
compare the right feature quantity with the left feature quantity and determine a rehabilitation progress of the subject based on the comparison, the comparison indicating consistency among the unit column vectors $W_1^{(1)}, W_2^{(1)}, \ldots, W_p^{(1)}$, consistency among the unit column vectors $W_1^{(2)}, W_2^{(2)}, \ldots, W_p^{(2)}$, consistency among the unit column vectors $W_1^{(n)}, W_2^{(n)}, \ldots, W_p^{(n)}$, these unit column vectors $W_1^{(1)}, W_2^{(1)}, \ldots, W_p^{(1)}$, unit column vectors $W_1^{(2)}, W_2^{(2)}, \ldots, W_p^{(2)}, \ldots$, and unit column vectors $W_1^{(n)}, W_2^{(n)}, \ldots, W_p^{(n)}$ being included in the calculated muscle synergy matrices $W_1, W_2, \ldots, W_p$; and
provide the subject with feedback of progress of training based on the comparison between the right feature quantity and the left feature quantity, the feedback of progress being used to efficiently assess the rehabilitation progress, wherein providing the subject with feedback of progress of training includes applying electrical stimulation to a portion of the body of the subject.

5. The training apparatus according to claim 4, wherein the processor is configured to apply non-negative matrix factorization, and
the left feature quantity and the right feature quantity are each an SSI that are calculated through computation of correlation coefficient r(x,y) of vectors x, y according to Expression II:

$$SSI = 2/[n \times p(p-1)] \times \Sigma_{i=1}^{n} \Sigma_{k=1}^{p} \Sigma_{h=1}^{p}{}_{,h \neq k} r(W_k^{(i)}, W_h^{(j)}).\quad \text{Expression II:}$$

6. The training apparatus according to claim 5, wherein the processor is configured to output, to the subject, one of a fact that the SSI is larger than or equal to a predetermined threshold and a fact that the SSI tends to increase with an increase in the p indicating the number of the behaviors.

7. A training apparatus for rehabilitation, the apparatus comprising a processor configured to:
simultaneously measure time-series myoelectric potentials of each of muscles 1, 2, ..., m for a right side of a body of a subject while measuring the time-series myoelectric potentials for a left side of the body of the subject while the subject is performing a task consisting of different behaviors k=1, 2, ..., p, the task including bending and stretching a right wrist and a left wrist of the subject;
calculate a muscle synergy matrix $W_k$, a control matrix $C_k$ and an error matrix $E_k$ based on the acquired time-series myoelectric potentials and from a myoelectric potential matrix $M_k$ for each of the behaviors k=1, 2, ..., p so that a relationship $M_k = W_k C_k + E_k$ is satisfied,
  row vectors each expressing the acquired time-series myoelectric potentials of a corresponding one of the muscles 1, 2, ..., m being arranged in rows in the myoelectric potential matrix $M_k$, n unit column vectors $W_k^{(1)}, W_k^{(2)}, \ldots, W_k^{(n)}$ being arranged in columns in the muscle synergy matrix $W_k$, n row vectors $C_k^{(1)}, C_k^{(2)}, \ldots, C_k^{(n)}$ being arranged in rows in the control matrix $C_k$;
calculate a right feature quantity for a muscle of the right side of the body of the subject and a left feature quantity for a muscle of the left side of the body of the subject, the muscle of the right side of the body and the muscle of the left side of the body being selected from the muscles 1, 2, ... m;
compare the right feature quantity with the left feature quantity and determine a rehabilitation progress of the subject based on the comparison, the comparison indicating consistency among the row vectors $C_1^{(1)}, C_2^{(1)}, \ldots, C_p^{(1)}$, consistency among the row vectors $C_1^{(2)}, C_2^{(2)}, \ldots, C_p^{(2)}, \ldots$, consistency among the row vectors $C_1^{(n)}, C_2^{(n)}, \ldots, C_p^{(n)}, \ldots$, these row vectors $C_1^{(1)}, C_2^{(1)}, \ldots, C_p^{(1)}$, row vectors $C_1^{(2)}, C_2^{(2)}, \ldots, C_p^{(2)}, \ldots$, and row vectors $C_1^{(n)}, C_2^{(n)}, \ldots, C_p^{(n)}$ being included in the calculated control matrices $C_1, C_2, \ldots, C_p$; and
provide the subject with feedback of progress of training based on the comparison between the right feature quantity and the left feature quantity, the feedback of progress being used to efficiently assess the rehabilitation progress, wherein providing the subject with feedback of progress of training includes applying electrical stimulation to a portion of the body of the subject.

8. The training apparatus according to claim 7, wherein the processor is configured to apply non-negative matrix factorization, and
the left feature quantity and the right feature quantity are each an $SSI_C$ that are calculated through computation of correlation coefficient r(x,y) of vectors x, y according to Expression III:

$$SSI_C = 2/[n \times p(p-1)] \times \Sigma_{i=1}^{n} \Sigma_{k=1}^{p} \Sigma_{h=1}^{p}{}_{,h \neq k} r(C_k^{(i)}, C_h^{(j)})\quad \text{Expression III:}$$

9. The training apparatus according to claim 8, wherein the processor is configured to output, to the subject, one of the fact that the $SSI_C$ is smaller than or equal to a predetermined threshold and the fact that the $SSI_C$ tends to decrease with an increase in the p indicating the number of the behaviors.

10. A training method for a rehabilitation apparatus, the training method comprising:
simultaneously measuring time-series myoelectric potentials of each of muscles 1, 2, ..., m for a right side of a body of a subject while measuring the time-series myoelectric potentials for a left side of the body of the subject while the subject is performing different behaviors, the different behaviors being included in a task including bending and stretching a right wrist and a left wrist of the subject;
calculating a muscle synergy matrix W, a control matrix C and an error matrix E based on the acquired time-series myoelectric potentials and from a myoelectric potential matrix M so that a relationship M=WC+E is satisfied,
  row vectors each expressing the acquired time-series myoelectric potentials of a corresponding one of the muscles 1, 2, ..., m being arranged in rows in the myoelectric potential matrix M, n unit column vectors $W^{(1)}, W^{(2)}, \ldots, W^{(n)}$ being arranged in columns in the muscle synergy matrix W, n row vectors $C^{(1)}, C^{(2)}, \ldots, C^{(n)}$ being arranged in rows in the control matrix C;

calculating a right feature quantity for a muscle of the right side of the body of the subject and a left feature quantity for a muscle of the left side of the body of the subject, the muscle of the right side of the body and the muscle of the left side of the body being selected from the muscles 1, 2, ... m;

comparing the right feature quantity with the left feature quantity and determining a rehabilitation progress of the subject based on the comparison, the comparison indicating consistency among the unit column vectors $W^{(1)}, W^{(2)}, \ldots, W^{(n)}$ included in the calculated muscle synergy matrix W; and providing the subject with feedback of progress of training based on the comparison between the right feature quantity and the left feature quantity, the feedback of progress of training being used to efficiently assess the rehabilitation progress, wherein providing the subject with feedback of progress of training includes applying electrical stimulation to a portion of the body of the subject.

11. A training method for a rehabilitation apparatus, the training method comprising:

simultaneously measuring time-series myoelectric potentials of each of muscles 1, 2, ..., m for a right side of a body of a subject while measuring the time-series myoelectric potentials for a left side of the body of the subject while the subject is performing a task consisting of different behaviors k=1, 2, ..., p, the task including bending and stretching a right wrist and a left wrist of the subject;

calculating a muscle synergy matrix $W_k$, a control matrix $C_k$ and an error matrix $E_k$ based on the acquired time-series myoelectric potentials and from a myoelectric potential matrix $M_k$ for each of the behaviors k=1, 2, ..., p so that a relationship $M_k = W_k C_k + E_k$ is satisfied, row vectors each expressing the acquired time-series myoelectric potentials of a corresponding one of the muscles 1, 2, ..., m being arranged in rows in the myoelectric potential matrix $M_k$, n unit column vectors $W_k^{(1)}, W_k^{(2)}, \ldots, W_k^{(n)}$ being arranged in columns in the muscle synergy matrix $W_k$, n row vectors $C_k^{(1)}, C_k^{(2)}, \ldots, C_k^{(n)}$ being arranged in rows in the control matrix $C_k$;

calculating a right feature quantity for a muscle of the right side of the body of the subject and a left feature quantity for a muscle of the left side of the body of the subject, the muscle of the right side of the body and the muscle of the left side of the body being selected from the muscles 1, 2, ... m;

comparing the right feature quantity with the left feature quantity and determining a rehabilitation progress of the subject based on the comparison, the comparison indicating consistency among the unit column vectors $W_1^{(1)}, W_2^{(1)}, \ldots, W_p^{(1)}$, consistency among the unit column vectors $W_1^{(2)}, W_2^{(2)}, \ldots, W_p^{(2)}, \ldots$, consistency among the unit column vectors $W_1^{(n)}, W_2^{(n)}, \ldots, W_p^{(n)}$, these unit column vectors $W_1^{(1)}, W_2^{(1)}, \ldots, W_p^{(1)}$, unit column vectors $W_1^{(2)}, W_2^{(2)}, \ldots, W_p^{(2)}, \ldots$, and unit column vectors $W_1^{(n)}, W_2^{(n)}, \ldots, W_p^{(n)}$ being included in the calculated muscle synergy matrices $W_1, W_2, \ldots, W_p$; and providing the subject with feedback of progress of training based on the comparison between the right feature quantity and the left feature quantity, the feedback of progress being used to efficiently assess the subject's rehabilitation progress, wherein providing the subject with feedback of progress of training includes applying electrical stimulation to a portion of the body of the subject.

12. A training method for a rehabilitation apparatus, the training method comprising:

simultaneously measuring time-series myoelectric potentials of each of muscles 1, 2, ..., m for a right side of a body of a subject while measuring the time-series myoelectric potentials for a left side of the body of the subject while the subject is performing a task consisting of different behaviors k=1, 2, ..., p, the task including bending and stretching a right wrist and a left wrist of the subject;

calculating a muscle synergy matrix $W_k$, a control matrix $C_k$ and an error matrix $E_k$ based on the acquired time-series myoelectric potentials and from a myoelectric potential matrix $M_k$ for each of the behaviors k=1, 2, ..., p so that a relationship $M_k = W_k C_k + E_k$ is satisfied, row vectors each expressing the acquired time-series myoelectric potentials of a corresponding one of the muscles 1, 2, ..., m being arranged in rows in the myoelectric potential matrix $M_k$, n unit column vectors $W_k^{(1)}, W_k^{(2)}, \ldots, W_k^{(n)}$ being arranged in columns in the muscle synergy matrix $W_k$, n row vectors Ck(1), Ck(2), ..., Ck(n) being arranged in rows in the control matrix Ck;

calculating a right feature quantity for a muscle of the right side of the body of the subject and a left feature quantity for a muscle of the left side of the body of the subject, the muscle of the right side of the body and the muscle of the left side of the body being selected from the muscles 1, 2, ... m;

comparing the right feature quantity with the left feature quantity and determining a rehabilitation progress of the subject based on the comparison, the comparison indicating consistency among the row vectors $C_1^{(1)}, C_2^{(1)}, \ldots, C_p^{(1)}$, consistency among the row vectors $C_1^{(2)}, C_2^{(2)}, \ldots, C_p^{(2)}, \ldots$, consistency among the row vectors $C_1^{(n)}, C_2^{(n)}, \ldots, C_p^{(n)}, \ldots$, these row vectors $C_1^{(1)}, C_2^{(1)}, \ldots, C_p^{(1)}$, row vectors $C_1^{(2)}, C_2^{(2)}, \ldots, C_p^{(2)}, \ldots$, and row vectors $C_1^{(n)}, C_2^{(n)}, \ldots, C_p^{(n)}$ being included in the calculated control matrices $C_1, C_2, \ldots, C_p$; and providing the subject with feedback of progress of training based on the comparison between the right feature quantity and the left feature quantity, the feedback of progress being used to efficiently assess the rehabilitation progress, wherein providing the subject with feedback of progress of training includes applying electrical stimulation to a portion of the body of the subject.

* * * * *